(12) United States Patent
Goble et al.

(10) Patent No.: US 6,482,202 B1
(45) Date of Patent: *Nov. 19, 2002

(54) UNDER WATER TREATMENT

(75) Inventors: Nigel M. Goble, Berks (GB); Colin C. O. Goble, Surrey (GB)

(73) Assignee: Gyrus Medical Limited, Wales (GB)

( * ) Notice: Subject to any disclaimer, the term of this patent is extended or adjusted under 35 U.S.C. 154(b) by 26 days.

This patent is subject to a terminal disclaimer.

(21) Appl. No.: 09/756,676

(22) Filed: Jan. 10, 2001

Related U.S. Application Data (63) Continuation of application No. 09/202,025, filed as application No. PCT/GB97/01632 on Jun. 17, 1997, now Pat. No. 6,210,405.

(30) Foreign Application Priority Data

Jun. 20, 1996 (GB) ............................................. 9612993

(51) Int. Cl.[7] .............................................. A61B 18/18
(52) U.S. Cl. ......................... 606/41; 607/101; 607/105
(58) Field of Search ............................. 606/41, 42, 45, 606/48–50; 607/101, 102, 104, 105; 604/35, 114

(56) References Cited

U.S. PATENT DOCUMENTS

| | | |
|---|---|---|
| 164,184 A | 6/1875 | Kidder |
| 1,366,756 A | 1/1921 | Wappler |
| 1,735,271 A | 11/1929 | Groff |
| 1,814,791 A | 7/1931 | Ende |
| 1,889,609 A | 11/1932 | Mutscheller |
| 1,932,258 A | 10/1933 | Wappler |
| 1,943,543 A | 1/1934 | McFadden |
| 1,952,617 A | 3/1934 | Wappler |
| 1,983,669 A | 12/1934 | Kimble |
| 2,050,904 A | 8/1936 | Trice |

(List continued on next page.)

FOREIGN PATENT DOCUMENTS

| | | |
|---|---|---|
| CH | 243478 | 7/1946 |
| DE | 651428 | 9/1937 |
| DE | 1007960 | 5/1957 |
| DE | 2222820 | 11/1973 |
| DE | 2457900 | 5/1976 |
| DE | 2930982 | 2/1981 |
| DE | 3209444 | 10/1982 |
| DE | 3215832 A | 11/1982 |

(List continued on next page.)

OTHER PUBLICATIONS

Cook, Albert M. & John G. Webster, *Therapeutic Medical Devices Application and Design,* Prentice–Hall Inc., New Jersey, 1982, p. 349.

Pearce, John A., *Electrosurgery,* John Wiley & Sons Inc., New York, 1986, pp. 17, 69–75 and 87.

Wyeth, G.A., *Electrosurgical Unit,* pp. 1180–1202.

(List continued on next page.)

*Primary Examiner*—Michael Peffley
(74) *Attorney, Agent, or Firm*—Nixon & Vanderhye, P.C.

(57) ABSTRACT

An electrosurgical instrument, which is used for the treatment of tissue in the presence of an electrically-conductive fluid medium, comprises an instrument shaft, and an electrode assembly at one end of the shaft. The electrode assembly comprises a tissue treatment electrode and a return electrode which is electrically insulated from the tissue treatment electrode by means of an insulation member. The tissue treatment electrode has an exposed end for treating tissue, and the return electrode has a fluid contact surface which is spaced from the tissue treatment electrode in such a manner as to define, in use, a conductive fluid path that completes an electrical circuit between the tissue treatment electrode and the return electrode. The electrode assembly is provided with a plurality of apertures in the region of the tissue treatment electrode, through which apertures vapour bubbles and/or particulate material can be aspirated from the region surrounding the tissue treatment electrode.

11 Claims, 3 Drawing Sheets

U.S. PATENT DOCUMENTS

| | | |
|---|---|---|
| 2,056,377 A | 10/1936 | Wappler |
| 2,196,171 A | 4/1940 | Arnesen |
| 2,888,928 A | 6/1959 | Seiger |
| 3,035,580 A | 5/1962 | Guiorguiev |
| 3,460,539 A | 8/1969 | Anhalt, Sr. |
| 3,595,239 A | 7/1971 | Petersen |
| 3,601,126 A | 8/1971 | Estes |
| 3,614,414 A | 10/1971 | Gores |
| 3,648,001 A | 3/1972 | Anderson et al. |
| 3,685,518 A | 8/1972 | Beurle et al. |
| 3,699,967 A | 10/1972 | Anderson |
| 3,707,149 A | 12/1972 | Hao et al. |
| 3,801,766 A | 4/1974 | Morrison, Jr. |
| 3,815,604 A | 6/1974 | O'Malley et al. |
| 3,845,771 A | 11/1974 | Vise |
| 3,847,153 A | 11/1974 | Weissman |
| 3,870,047 A | 3/1975 | Gonser |
| 3,885,569 A | 5/1975 | Judson |
| 3,898,991 A | 8/1975 | Ikuno et al. |
| 3,901,242 A | 8/1975 | Storz |
| 3,902,494 A | 9/1975 | Haberlen et al. |
| 3,903,891 A | 9/1975 | Brayshaw |
| 3,920,021 A | 11/1975 | Hiltebrandt |
| 3,920,022 A | 11/1975 | Pastor |
| 3,923,063 A | 12/1975 | Andrews et al. |
| 3,929,137 A | 12/1975 | Gonser et al. |
| 3,939,839 A | 2/1976 | Curtiss |
| 3,945,375 A | 3/1976 | Banko |
| 3,963,030 A | 6/1976 | Newton |
| 3,964,487 A | 6/1976 | Judson |
| 3,970,088 A | 7/1976 | Morrison |
| 3,974,833 A | 8/1976 | Durden, III |
| 4,011,872 A | 3/1977 | Komiya |
| 4,016,881 A | 4/1977 | Rioux et al. |
| 4,024,467 A | 5/1977 | Andrews et al. |
| 4,033,351 A | 7/1977 | Hetzel |
| 4,040,426 A | 8/1977 | Morrison, Jr. |
| 4,043,342 A | 8/1977 | Morrison, Jr. |
| 4,051,855 A | 10/1977 | Schneiderman |
| 4,060,088 A | 11/1977 | Morrison, Jr. et al. |
| 4,069,827 A | 1/1978 | Dominy |
| 4,074,718 A | 2/1978 | Morrison, Jr. |
| 4,092,986 A | 6/1978 | Schneiderman |
| 4,114,623 A | 9/1978 | Meinke et al. |
| 4,116,198 A | 9/1978 | Roos |
| 4,119,102 A | 10/1978 | LeVeen |
| 4,126,137 A | 11/1978 | Archibald |
| 4,154,240 A | 5/1979 | Ikuno et al. |
| 4,189,685 A | 2/1980 | Doss |
| 4,200,104 A | 4/1980 | Harris |
| 4,202,337 A | 5/1980 | Hren et al. |
| 4,204,549 A | 5/1980 | Paglione |
| 4,210,152 A | 7/1980 | Berry |
| 4,228,800 A | 10/1980 | Degler, Jr. et al. |
| 4,248,231 A | 2/1981 | Herczog et al. |
| 4,271,837 A | 6/1981 | Schuler |
| 4,281,373 A | 7/1981 | Mabille |
| 4,301,802 A | 11/1981 | Poler |
| 4,326,529 A | 4/1982 | Doss et al. |
| 4,346,332 A | 8/1982 | Walden |
| 4,376,263 A | 3/1983 | Pittroff et al. |
| 4,381,007 A | 4/1983 | Doss |
| 4,416,277 A | 11/1983 | Newton et al. |
| 4,418,692 A | 12/1983 | Guay |
| 4,429,698 A | 2/1984 | Bentall |
| 4,448,198 A | 5/1984 | Turner |
| 4,474,179 A | 10/1984 | Koch |
| 4,476,862 A | 10/1984 | Pao |
| 4,492,231 A | 1/1985 | Auth |
| 4,494,541 A | 1/1985 | Archibald |
| 4,512,338 A | 4/1985 | Balko et al. |
| 4,517,976 A | 5/1985 | Murakoshi et al. |
| 4,524,770 A | 6/1985 | Orandi |
| 4,532,924 A | 8/1985 | Auth et al. |
| 4,534,347 A | 8/1985 | Taylor |
| 4,548,207 A | 10/1985 | Reimels |
| 4,559,943 A | 12/1985 | Bowers |
| 4,559,951 A | 12/1985 | Dahl et al. |
| 4,562,838 A | 1/1986 | Walker |
| 4,565,200 A | 1/1986 | Cosman |
| 4,567,890 A | 2/1986 | Ohta et al. |
| 4,580,557 A | 4/1986 | Hertzmann |
| 4,590,934 A | 5/1986 | Malis et al. |
| 4,593,691 A | 6/1986 | Lindstrom et al. |
| 4,617,927 A | 10/1986 | Manes |
| 4,657,015 A | 4/1987 | Irnich |
| 4,658,819 A | 4/1987 | Harris et al. |
| 4,658,820 A | 4/1987 | Klicek |
| 4,669,468 A | 6/1987 | Cartmell et al. |
| 4,674,499 A * | 6/1987 | Pao .............................. 604/20 |
| 4,681,122 A | 7/1987 | Winters et al. |
| 4,682,596 A | 7/1987 | Bales et al. |
| 4,688,569 A | 8/1987 | Rabinowitz |
| 4,696,668 A | 9/1987 | Wilcox |
| 4,706,667 A | 11/1987 | Roos |
| 4,709,698 A | 12/1987 | Johnston et al. |
| 4,712,544 A | 12/1987 | Ensslin |
| 4,727,874 A | 3/1988 | Bowers et al. |
| 4,735,201 A | 4/1988 | O'Reilly |
| 4,769,005 A | 9/1988 | Ginsburg et al. |
| 4,781,175 A | 11/1988 | McGreevy et al. |
| 4,799,480 A | 1/1989 | Abraham et al. |
| 4,800,899 A | 1/1989 | Elliott |
| 4,802,476 A | 2/1989 | Noerenberg et al. |
| 4,805,616 A | 2/1989 | Pao |
| 4,813,429 A | 3/1989 | Eshel et al. |
| 4,820,298 A | 4/1989 | Leveen et al. |
| 4,823,791 A | 4/1989 | D'Amelio et al. |
| 4,827,927 A | 5/1989 | Newton |
| 4,832,048 A | 5/1989 | Cohen |
| 4,850,353 A | 7/1989 | Stasz et al. |
| 4,860,744 A | 8/1989 | Johnson et al. |
| 4,878,493 A | 11/1989 | Pasternak et al. |
| 4,886,074 A | 12/1989 | Bisping |
| 4,919,129 A | 4/1990 | Weber, Jr. et al. |
| 4,920,978 A | 5/1990 | Colvin |
| 4,931,047 A | 6/1990 | Broadwin et al. |
| 4,936,281 A | 6/1990 | Stasz |
| 4,936,301 A | 6/1990 | Rexroth et al. |
| 4,936,310 A | 6/1990 | Engstrom et al. |
| 4,936,842 A | 6/1990 | D'Amelio et al. |
| 4,943,290 A | 7/1990 | Rexroth et al. |
| 4,950,267 A | 8/1990 | Ishihara et al. |
| 4,955,377 A | 9/1990 | Lennox et al. |
| 4,966,597 A | 10/1990 | Cosman |
| 4,967,765 A | 11/1990 | Turner et al. |
| 4,969,885 A | 11/1990 | Farin |
| 4,976,711 A | 12/1990 | Parins et al. |
| 4,994,069 A | 2/1991 | Ritchart et al. |
| 4,998,933 A | 3/1991 | Eggers et al. |
| 5,007,908 A | 4/1991 | Rydell |
| 5,009,656 A | 4/1991 | Reimels |
| 5,013,312 A | 5/1991 | Parins et al. |
| 5,019,076 A | 5/1991 | Yamanashi et al. |
| 5,035,696 A | 7/1991 | Rydell |
| 5,037,379 A | 8/1991 | Clayman et al. |
| 5,047,027 A | 9/1991 | Rydell |
| 5,047,206 A | 9/1991 | Rydell |
| 5,057,107 A | 10/1991 | Parins et al. |
| 5,062,031 A | 10/1991 | Flachenecker et al. |
| 5,071,418 A | 12/1991 | Rosenbaum |

| Patent No. | Date | Name |
|---|---|---|
| 5,080,660 A | 1/1992 | Buelna |
| 5,083,565 A | 1/1992 | Parins |
| 5,085,659 A | 2/1992 | Rydell |
| 5,088,997 A | 2/1992 | Delahuerga et al. |
| 5,098,431 A | 3/1992 | Rydell |
| 5,099,840 A | 3/1992 | Goble et al. |
| 5,108,391 A | 4/1992 | Flachenecker et al. |
| 5,108,407 A | 4/1992 | Geremia et al. |
| RE33,925 E | 5/1992 | Bales et al. |
| 5,117,978 A | 6/1992 | Blumenfeld et al. |
| 5,122,138 A | 6/1992 | Manwaring |
| 5,133,365 A | 7/1992 | Heil, Jr. et al. |
| 5,158,561 A | 10/1992 | Rydell et al. |
| 5,167,658 A | 12/1992 | Ensslin |
| 5,167,659 A | 12/1992 | Ohtomo et al. |
| 5,171,255 A | 12/1992 | Rydell |
| 5,171,311 A | 12/1992 | Rydell et al. |
| 5,178,620 A | 1/1993 | Eggers et al. |
| 5,190,517 A | 3/1993 | Zieve et al. |
| 5,195,959 A | 3/1993 | Smith |
| 5,196,007 A | 3/1993 | Ellman et al. |
| 5,197,963 A | 3/1993 | Parins |
| 5,201,743 A | 4/1993 | Haber et al. |
| 5,207,675 A | 5/1993 | Canady |
| 5,217,457 A | 6/1993 | Delahuerga et al. |
| 5,217,458 A | 6/1993 | Parins |
| 5,217,459 A | 6/1993 | Kamerling |
| 5,221,281 A | 6/1993 | Klicek |
| 5,244,462 A | 9/1993 | Delahuerga et al. |
| 5,249,585 A | 10/1993 | Turner et al. |
| 5,250,047 A | 10/1993 | Rydell |
| 5,258,006 A | 11/1993 | Rydell et al. |
| 5,259,395 A | 11/1993 | Li |
| 5,261,906 A | 11/1993 | Pennino et al. |
| 5,267,994 A | 12/1993 | Gentelia et al. |
| 5,267,997 A | 12/1993 | Farin et al. |
| 5,277,201 A | 1/1994 | Stern |
| 5,277,696 A * | 1/1994 | Hagen ................... 606/41 |
| 5,281,213 A | 1/1994 | Milder et al. |
| 5,281,216 A | 1/1994 | Klicek |
| 5,282,799 A | 2/1994 | Rydell |
| 5,282,845 A | 2/1994 | Bush et al. |
| 5,290,282 A | 3/1994 | Casscells |
| 5,290,283 A | 3/1994 | Suda |
| 5,300,068 A | 4/1994 | Rosar et al. |
| 5,300,069 A | 4/1994 | Hunsberger et al. |
| 5,300,070 A | 4/1994 | Gentelia et al. |
| 5,304,214 A | 4/1994 | DeFord et al. |
| 5,306,238 A | 4/1994 | Fleenor |
| 5,317,155 A | 5/1994 | King |
| 5,318,563 A | 6/1994 | Malis et al. |
| 5,320,627 A | 6/1994 | Sorensen et al. |
| 5,330,470 A | 7/1994 | Hagen |
| 5,330,471 A | 7/1994 | Eggers |
| 5,334,193 A | 8/1994 | Nardella |
| 5,334,198 A | 8/1994 | Hart et al. |
| 5,336,222 A | 8/1994 | Durgin, Jr. et al. |
| 5,342,357 A | 8/1994 | Nardella |
| 5,342,391 A | 8/1994 | Foshee et al. |
| 5,344,428 A | 9/1994 | Griffiths |
| 5,352,222 A | 10/1994 | Rydell |
| 5,354,296 A | 10/1994 | Turkel |
| 5,366,443 A | 11/1994 | Eggers et al. |
| 5,370,645 A | 12/1994 | Klicek et al. |
| 5,370,675 A | 12/1994 | Edwards et al. |
| 5,372,596 A | 12/1994 | Klicek et al. |
| 5,382,247 A | 1/1995 | Cimino et al. |
| 5,383,874 A | 1/1995 | Jackson et al. |
| 5,383,876 A | 1/1995 | Nardella |
| 5,383,917 A | 1/1995 | Desai et al. |
| 5,383,923 A | 1/1995 | Webster, Jr. |
| 5,395,363 A | 3/1995 | Billings et al. |
| 5,395,368 A | 3/1995 | Ellman et al. |
| 5,403,311 A | 4/1995 | Abele et al. |
| 5,419,767 A | 5/1995 | Eggers et al. |
| 5,422,567 A | 6/1995 | Matsunaga |
| 5,423,808 A | 6/1995 | Edwards et al. |
| 5,423,809 A | 6/1995 | Klicek |
| 5,423,810 A | 6/1995 | Goble et al. |
| 5,423,811 A | 6/1995 | Imran et al. |
| 5,431,649 A | 7/1995 | Mulier et al. |
| 5,437,662 A | 8/1995 | Nardella |
| 5,438,302 A | 8/1995 | Goble |
| 5,441,499 A | 8/1995 | Fritzsch |
| 5,443,470 A | 8/1995 | Stern et al. |
| 5,451,223 A * | 9/1995 | Ben-Simhon ................ 604/35 |
| 5,454,809 A | 10/1995 | Janssen |
| 5,462,521 A | 10/1995 | Brucker et al. |
| 5,472,441 A | 12/1995 | Edwards et al. |
| 5,472,443 A | 12/1995 | Cordis et al. |
| 5,480,397 A | 1/1996 | Eggers et al. |
| 5,480,398 A | 1/1996 | Eggers et al. |
| 5,496,312 A | 3/1996 | Klicek |
| 5,496,314 A | 3/1996 | Eggers |
| 5,505,728 A | 4/1996 | Ellman et al. |
| 5,505,730 A | 4/1996 | Edwards |
| 5,507,743 A | 4/1996 | Edwards et al. |
| 5,514,129 A | 5/1996 | Smith |
| 5,514,130 A | 5/1996 | Baker |
| 5,514,131 A | 5/1996 | Edwards et al. |
| 5,520,684 A | 5/1996 | Imran |
| 5,520,685 A | 5/1996 | Wojciechowicz |
| 5,522,815 A | 6/1996 | Durgin, Jr. et al. |
| 5,531,744 A | 7/1996 | Nardella et al. |
| 5,536,267 A | 7/1996 | Edwards et al. |
| 5,540,680 A | 7/1996 | Guglielmi et al. |
| 5,540,681 A | 7/1996 | Strul et al. |
| 5,540,682 A | 7/1996 | Gardner et al. |
| 5,540,683 A | 7/1996 | Ichikawa et al. |
| 5,540,684 A | 7/1996 | Hassler, Jr. |
| 5,540,685 A | 7/1996 | Parins et al. |
| 5,542,916 A | 8/1996 | Hirsch et al. |
| 5,542,945 A | 8/1996 | Fritzsch |
| 5,545,161 A | 8/1996 | Imran |
| 5,545,193 A | 8/1996 | Fleischman et al. |
| 5,549,605 A | 8/1996 | Hahnen |
| 5,554,172 A | 9/1996 | Horner et al. |
| 5,555,618 A | 9/1996 | Winkler |
| 5,556,396 A | 9/1996 | Cohen et al. |
| 5,556,397 A | 9/1996 | Long et al. |
| 5,558,671 A | 9/1996 | Yates |
| 5,562,720 A | 10/1996 | Stern et al. |
| 5,569,164 A | 10/1996 | Lurz |
| 5,569,242 A | 10/1996 | Lax et al. |
| 5,569,244 A | 10/1996 | Hahnen |
| 5,569,245 A | 10/1996 | Guglielmi et al. |
| 5,571,100 A | 11/1996 | Goble et al. |
| 5,575,789 A | 11/1996 | Bell et al. |
| 5,578,007 A | 11/1996 | Imran |
| 5,582,609 A | 12/1996 | Swanson et al. |
| 5,582,610 A | 12/1996 | Grossi et al. |
| 5,584,830 A | 12/1996 | Ladd et al. |
| 5,591,141 A | 1/1997 | Nettekoven |
| 5,599,344 A | 2/1997 | Paterson |
| 5,599,345 A | 2/1997 | Edwards et al. |
| 5,599,346 A | 2/1997 | Edwards et al. |
| 5,599,347 A | 2/1997 | Hart et al. |
| 5,599,348 A | 2/1997 | Gentelia et al. |
| 5,599,349 A | 2/1997 | D'Amelio |
| 5,603,711 A | 2/1997 | Parins et al. |
| 5,603,712 A | 2/1997 | Koranda et al. |
| 5,607,422 A | 3/1997 | Smeets et al. |

| | | | | | |
|---|---|---|---|---|---|
| 5,609,151 A | 3/1997 | Mulier et al. | DE | 4425015 | 1/1996 |
| 5,609,573 A | 3/1997 | Sandock | DE | 4429478 | 3/1996 |
| 5,611,798 A | 3/1997 | Eggers | DE | 19530004 A | 3/1996 |
| 5,620,481 A | 4/1997 | Desai et al. | DE | 19510185 A | 10/1996 |
| 5,624,439 A | 4/1997 | Edwards et al. | DE | 19512640 C2 | 10/1996 |
| 5,626,560 A | 5/1997 | Soring | DE | 19514552 A | 10/1996 |
| 5,626,575 A | 5/1997 | Crenner | DE | 19514553 C1 | 10/1996 |
| 5,626,576 A | 5/1997 | Janssen | DE | 19526243 C1 | 1/1997 |
| 5,626,578 A | 5/1997 | Tihon | DE | 19526244 | 1/1997 |
| 5,628,745 A | 5/1997 | Bek | DE | 19543547 C1 | 1/1997 |
| 5,628,771 A | 5/1997 | Mizukawa et al. | DE | 19620601 | 2/1997 |
| 5,630,426 A | 5/1997 | Eggers et al. | DE | 29617461 U | 2/1997 |
| 5,633,578 A | 5/1997 | Eggers et al. | DE | 19537897 A | 3/1997 |
| 5,634,924 A | 6/1997 | Turkel et al. | DE | 19542417 A | 5/1997 |
| 5,647,869 A | 7/1997 | Goble et al. | DE | 19542418 A | 5/1997 |
| 5,672,174 A | 9/1997 | Gough et al. | DE | 19542419 A | 5/1997 |
| 5,683,366 A | 11/1997 | Eggers et al. | DE | 19545539 A | 6/1997 |
| 5,693,045 A | 12/1997 | Eggers | DE | 19545756 A | 6/1997 |
| 5,697,281 A | 12/1997 | Eggers et al. | DE | 19650797 A | 6/1997 |
| 5,697,536 A | 12/1997 | Eggers et al. | EP | 0 013605 | 7/1980 |
| 5,697,882 A | 12/1997 | Eggers et al. | EP | 0 049633 | 4/1982 |
| 5,697,909 A | 12/1997 | Eggers et al. | EP | 0 067680 | 12/1982 |
| 5,700,262 A | 12/1997 | Acosta et al. | EP | 0 136855 | 4/1985 |
| 5,725,524 A | 3/1998 | Mulier et al. | EP | 0 219568 | 12/1985 |
| 5,735,846 A | 4/1998 | Panescu et al. | EP | 0 205851 | 12/1986 |
| 5,766,153 A | 6/1998 | Eggers et al. | EP | 0 280798 A | 9/1988 |
| 5,776,092 A | 7/1998 | Farin et al. | EP | 0 310431 | 4/1989 |
| 5,792,140 A | 8/1998 | Tu et al. | EP | 0 316469 | 5/1989 |
| 5,810,764 A | 9/1998 | Eggers et al. | EP | 0 325456 | 7/1989 |
| 5,810,809 A | 9/1998 | Rydell | EP | 0 332308 | 9/1989 |
| 5,830,214 A | 11/1998 | Flom et al. | EP | 0 373670 | 6/1990 |
| 5,833,689 A | 11/1998 | Long | EP | 0 392837 | 10/1990 |
| 5,843,019 A | 12/1998 | Eggers et al. | EP | 0 407057 | 1/1991 |
| 5,860,951 A | 1/1999 | Eggers et al. | EP | 0 412426 | 2/1991 |
| 5,871,469 A | 2/1999 | Eggers et al. | EP | 0 437377 | 7/1991 |
| 5,873,855 A | 2/1999 | Eggers et al. | EP | 0 448798 | 10/1991 |
| 5,888,198 A | 3/1999 | Eggers et al. | EP | 0 499491 | 8/1992 |
| 5,891,095 A | 4/1999 | Eggers et al. | EP | 0 507622 | 10/1992 |
| 5,902,272 A | 5/1999 | Eggers et al. | EP | 0 509670 | 10/1992 |
| 5,904,681 A | 5/1999 | West, Jr. | EP | 0 517243 | 12/1992 |
| 5,919,188 A | 7/1999 | Shearon et al. | EP | 0 518230 | 12/1992 |
| 5,919,191 A | 7/1999 | Lennox et al. | EP | 0 530400 | 3/1993 |
| 5,941,876 A | 8/1999 | Nardella et al. | EP | 0 536440 | 4/1993 |
| 5,944,715 A * | 8/1999 | Goble et al. .............. 606/41 | EP | 0 558316 | 9/1993 |
| 6,093,186 A | 7/2000 | Goble | EP | 0 558318 | 9/1993 |
| 6,210,405 B1 * | 4/2001 | Goble et al. .............. 606/41 | EP | 0 647435 | 4/1995 |
| | | | EP | 0 653192 | 5/1995 |

FOREIGN PATENT DOCUMENTS

| | | | | | |
|---|---|---|---|---|---|
| | | | EP | 0 674909 | 10/1995 |
| DE | 3119735 | 1/1983 | EP | 0 684015 | 11/1995 |
| DE | 3245570 | 6/1984 | EP | 0 688536 | 12/1995 |
| DE | 222207 | 5/1985 | EP | 0 692224 | 1/1996 |
| DE | 3423356 | 1/1986 | EP | 0 694290 | 1/1996 |
| DE | 3427517 | 1/1986 | EP | 0 697199 | 2/1996 |
| DE | 3511107 | 10/1986 | EP | 0 709065 | 5/1996 |
| DE | 3623688 | 1/1987 | EP | 0 714635 | 6/1996 |
| DE | 3530335 | 3/1987 | EP | 0 717967 | 6/1996 |
| DE | 3707820 | 9/1987 | EP | 0 732080 | 9/1996 |
| DE | 3622337 C2 | 1/1988 | EP | 0 733345 | 9/1996 |
| DE | 3642077 C2 | 6/1988 | EP | 0 737447 | 10/1996 |
| DE | 3708801 C2 | 9/1988 | EP | 0 740926 | 11/1996 |
| DE | 3824913 | 2/1990 | EP | 0 754437 | 1/1997 |
| DE | 3838840 C2 | 5/1990 | FR | 57862 | 9/1953 |
| DE | 3930451 | 3/1991 | FR | 1215305 | 4/1960 |
| DE | 4108269 C2 | 6/1992 | FR | 1454773 | 10/1966 |
| DE | 4103972 C2 | 8/1992 | FR | 2313949 | 1/1977 |
| DE | 4126608 | 2/1993 | FR | 2443829 | 7/1980 |
| DE | 4139029 C2 | 6/1993 | FR | 2501034 | 9/1982 |
| DE | 4217999 A1 | 12/1993 | GB | 1361497 | 7/1974 |
| DE | 4237321 A1 | 5/1994 | GB | 2037167 | 7/1980 |
| DE | 4323585 | 1/1995 | GB | 1583397 | 1/1981 |
| DE | 4339049 | 5/1995 | GB | 2133290 | 7/1984 |

| | | |
|---|---|---|
| GB | 2145932 | 4/1985 |
| GB | 2161081 | 1/1986 |
| GB | 2164473 | 3/1986 |
| GB | 2177309 | 1/1987 |
| GB | 2179861 | 3/1987 |
| GB | 2213381 | 8/1989 |
| GB | 2214430 | 9/1989 |
| JP | 62211060 | 9/1987 |
| SU | 644491 | 1/1979 |
| WO | WO 81/03271 | 11/1981 |
| WO | WO 82/00084 | 1/1982 |
| WO | WO 82/02488 | 8/1982 |
| WO | WO 84/03829 | 10/1984 |
| WO | WO 88/01851 | 3/1988 |
| WO | WO 90/03152 | 4/1990 |
| WO | WO 93/08756 | 5/1993 |
| WO | WO 93/13718 | 7/1993 |
| WO | WO 93/13816 | 7/1993 |
| WO | WO 93/16650 | 9/1993 |
| WO | WO 93/19681 | 10/1993 |
| WO | WO 93/19682 | 10/1993 |
| WO | WO 93/20747 | 10/1993 |
| WO | WO 93/20877 | 10/1993 |
| WO | WO 94/04220 | 3/1994 |
| WO | WO 94/06510 | 3/1994 |
| WO | WO 94/10921 | 5/1994 |
| WO | WO 94/10924 | 5/1994 |
| WO | WO 94/10925 | 5/1994 |
| WO | WO 94/23659 | 10/1994 |
| WO | WO 94/26228 | 11/1994 |
| WO | WO 94/28809 | 12/1994 |
| WO | WO 95/02369 | 1/1995 |
| WO | WO 95/05781 | 3/1995 |
| WO | WO 95/09576 | 4/1995 |
| WO | WO 95/09577 | 4/1995 |
| WO | WO 95/10320 | 4/1995 |
| WO | WO 95/10321 | 4/1995 |
| WO | WO 95/17855 | 7/1995 |
| WO | WO 95/18575 | 7/1995 |
| WO | WO 95/19733 | 7/1995 |
| WO | WO 95/20360 | 8/1995 |
| WO | WO 95/23558 | 9/1995 |
| WO | WO 95/24160 | 9/1995 |
| WO | WO 95/25472 | 9/1995 |
| WO | WO 95/26686 | 10/1995 |
| WO | WO 95/30377 | 11/1995 |
| WO | WO 95/31144 | 11/1995 |
| WO | WO 96/00036 | 1/1996 |
| WO | WO 96/00039 | 1/1996 |
| WO | WO 96/00040 | 1/1996 |
| WO | WO 96/00042 | 1/1996 |
| WO | WO 96/00043 | 1/1996 |
| WO | WO 96/00528 | 1/1996 |
| WO | WO 96/04859 | 2/1996 |
| WO | WO 96/07360 | 3/1996 |
| WO | WO 96/09010 | 3/1996 |
| WO | WO 96/10367 | 4/1996 |
| WO | WO 96/14020 | 5/1996 |
| WO | WO 96/14021 | 5/1996 |
| WO | WO 96/18349 | 6/1996 |
| WO | WO 96/19152 | 6/1996 |
| WO | WO 96/23448 | 8/1996 |
| WO | WO 96/23449 | 8/1996 |
| WO | WO 96/24296 | 8/1996 |
| WO | WO 96/24301 | 8/1996 |
| WO | WO 96/27337 | 9/1996 |
| WO | WO 96/29946 | 10/1996 |
| WO | WO 96/32897 | 10/1996 |
| WO | WO 96/34567 | 11/1996 |
| WO | WO 96/34569 | 11/1996 |
| WO | WO 96/34570 | 11/1996 |
| WO | WO 96/34571 | 11/1996 |
| WO | WO 96/37146 | 11/1996 |
| WO | WO 96/38094 | 12/1996 |
| WO | WO 96/39085 | 12/1996 |
| WO | WO 96/39086 | 12/1996 |
| WO | WO 96/39088 | 12/1996 |
| WO | WO 96/39089 | 12/1996 |
| WO | WO 96/39966 | 12/1996 |
| WO | WO 96/39967 | 12/1996 |
| WO | WO 97/00646 | 1/1997 |
| WO | WO 97/00647 | 1/1997 |
| WO | WO 97/24993 | 7/1997 |
| WO | WO 98/00070 | 1/1998 |
| WO | WO 98/14131 | 4/1998 |

OTHER PUBLICATIONS

Everest Medical Technologies, Inc., "Everest Bipolar Laparoscopic Cholecystectomy," Transcript of Lecture by Dr. Olsen, Oct. 7, 1991.

Dobbie, A.K., "The Electrical Aspects of Surgical Diathermy," Biomedical Engineering, May 1969, pp. 206–216.

Valleylab, Excerpts from Valleylab SSE2L Instruction Manual, Valleylab Part No. A 945 110 005 H, Jan. 6, 1983.

Schurr, M. O. et al., "Histologic Effects of Different Technologies for Dissection in Endoscopic Surgery:Nd:YAG Laser, High Frequency and Water–Jet," End. Surg., vol. 2, 1994, pp. 195–201.

Newman, Laura, "Could Twist on TURP Knock Lasers Out," Urology Times, vol. 3, No. 3, Mar. 1995, p. 21.

ArthroCare Corporation, "The Arthrocare Arthroscopic System," 1995.

Tucker, R.D. et al., "In Vivo Effect of 5 French Bipolar and Monopolar Electro–Surgical Probes on Porcine Bladder," Urological Research, Springer–Verlag 1990, 18:291–294.

Kramolowsky, Eugene V. et al., "The Urological Application of Electrosurgery," The Journal of Urology, vol. 146, Sep. 1991, pp. 669–674.

Tucker, Robert D. et al., "A Comparison of Urologic Application of Bipolar Versus Monopolar Five French Electrosurgical Probes," The Journal of Urology, vol. 141, Mar. 1989, pp. 662–665.

Kramolowsky, Eugene V. et al., "Use of 5F Bipolar Electrosurgical Probe in Endoscopic Urological Procedures," The Journal of Urology, vol. 143, Feb. 1990, pp. 275–277.

Tucker, Robert et al., "A Bipolar Electrosurgical TURP Loop," Abstract of Paper P14–11, $7^{th}$ World Congress on Endourology and ESWL, Nov. 27–30, Kyoto, Japan, 1989, p. 248.

Ramsay, J.W. A. et al., "A Comparison of Bipolar and Monopolar Diathermy Probes in Experimental Animals," Urological Research, Springer–Verlag 1985, 13:99–102.

German Article w/ Translation: Elsasser, E. and Roos, E., "Concerning an Instrument for Transurethral Resection without Leakage of Current," Medizinal–Marks/Acta Medicotechnica, vol. 24, No. 4, 1976, pp. 129–134.

Nardella, Paul C., "Radio Frequency Energy and Impedance Feedback," SPIE, vol. 1068, Catheter–Based Sensing & Imaging Technology, 1989, pp. 42–48.

Honig, William M., "The Mechanism of Cutting in Electrosurgery," IEEE Transactions on Biomedical Engineering, Jan. 1975, pp. 58–65.

Barry, Kevin J. et al., "The Effect of Radiofrequency–Generated Thermal Energy on the Mechanical and Histologic Characteristics of the Arterial Wall In Vivo: Implications for Radiofrequency Angioplasty," American Heart Journal, vol. 117, No. 2, Feb. 1989, pp. 332–341.

Slager, Cornelis J. et al., "Vaporization of Atherosclerotic Plaques by Spark Erosion," Journal of American College of Cardiology, 1985, pp. 1382–1386.

Lee, Benjamin I. et al., "Thermal Compression and Molding of Atherosclerotic Vascular Tissue with Use of Radiofrequency Energy: Implications for Radiofrequency Balloon Angioplasty," Journal of American College of Cardiology, vol. 13, No. 5, Apr. 1989, pp. 1167–1175.

Piercey, J.R.A. et al., "Electrosurgical Treatment of Experimental Bleeding Canine Gastric Ulcers," Gastroenterology, vol. 74, No. 3, 1978, pp. 527–534.

Protell, Robert L. et al., "Computer–Assisted Electrocoagulation: Bipolar vs. Monopolar in the Treatment of Experimental Canine Gastric Ulcer Bleeding," Gastroenterology, vol. 80, No. 3, 1981, pp. 451–455.

Johnston, James H. et al., "Experimental Comparison of Endoscopic Yttrium–Aluminum–Garnet Laser, Electrosurgery, and Heater Probe for Canine Gut Arterial Coagulation," Gastroenterology, vol. 92, No. 5, May 1987, pp. 1101–1108.

Dennis, M.B. et al., "Evaluation of Electrofulguration in Control of Bleeding of Experimental Gastric Ulcers," Digestive Diseases and Sciences, vol. 24, No. 11, Nov. 1979, pp. 845–848.

Silverstein, Fred E. et al., "Endoscopic Hemostasis Using Laser Photocoagulation and Electrocoagulation," Digestive Diseases and Sciences, vol. 26, No. 7, July Supplement 1981, pp. 31s–40s.

Auth, D.C., "Animal Testing of Endoscopic Hemostasis with Lasers and Other Devices," Endoscopy, vol. 18, Supplement 2, May 1986, pp. 36–39.

McLean, A. J., "The Bovie Electrosurgical Current Generator—Some Underlying Principles and Results," Archives of Surgery, vol. 18, 1929, pp. 1863–1873.

McLean, A. J., "Characteristics of Adequate Electrosurgical Current," American Journal of Surgery, vol. XVIII, No. 3, Feb. 16, 1932, pp. 417–441.

Wattiez, Arnaud et al., *Electrosurgery in Operative Endoscopy*, Blackwell Science Ltd., London, 1995, pp. 87–93, 155–163.

Farin, G., "Pneumatically Controlled Bipolar Cutting Instrument," End. Surg., 1993, pp. 1–3.

Muller, W., "The Advantages of Laparoscopic Assisted Bipolar High–Frequency Surgery," End. Surg., 1993, pp. 1–6.

Reidenbach, H. D., "Fundamentals of Bipolar High–Frequency Surgery," End. Surg. 1993, pp. 85–90.

Penketh, Richard et al., "Clinical Evaluation of the Procision Bipolar Electrosurgical Generator During Laparoscopic Gynaecological Procedures," EAES, 2$^{nd}$ International Congress of the European Association for Endoscopic Surgery, Madrid, Sep. 15–17, 1994.

Lloyd, David M. et al., "A New Portable Bipolar Generator–Use in Laparoscopic Cholecystectomy," EAES, 2$^{nd}$ International Congress of the European Association for Endoscopic Surgery, Madrid, Sep. 15–17, 1994.

Buchelt, Martin et al., "Excimer Laser Ablation of Fibrocartilage: An In Vitro and In Vivo Study," Lasers in Surgery and Medicine, vol. 11, 1991, pp. 271–279.

Srinivasan, R., "Ablation of Polymers and Biological Tissue by Ultraviolet Lasers," Science, vol. 234, Oct. 31, 1986, pp. 559–565.

Pearce, John A., "Chapter 3 Electrosurgery," *Handbook of Biomedical Engineering*, Ed. Jacob Kline, Academic Press, Inc., 1988, pp. 99–113.

Selikowitz, Stuart M. et al., "Electric Current and Voltage Recordings on the Myocardium During Electrosurgical Procedures in Canines," *Reprint from Surgery, Gynecology & Obstetrics*, Mar. 1987, vol. 164, pp. 219–224.

Tucker, Robert D. et al., "Demodulated Low Frequency Currents from Electrosurgical Procedures," Surgery, Gynecology & Obstetrics, Jul. 1984, vol. 159, pp. 39–43.

Lu, David Y. et al., "Electrical Thermal Angioplasty: Catheter Design Features, In Vitro Tissue Ablation Studies and In Vivo Experimental Findings," Am J Cardiol, vol. 60, 1987, pp. 1117–1122.

Malis, Leonard I., "Electrosurgery: Technical Note," J. Neurosurg., vol. 85, 1996, pp. 970–975.

Slager, C. J. et al., "Spark Erosion of Arteriosclerotic Plaques," Kardiologie, vol. 76, Suppl. 6, 1987, pp. 67–71.

Geddes, Leslie A., *Medical Device Accidents—With Illustrative Cases*, CRC Press, New York, 1998, p. 93 (commentary on Honig, William M., "The Mechanism of Cutting in Electrosurgery," IEEE Transactions on Biomedical Engineering, Jan. 1975, pp. 58–65).

Valleylab, Inc., "Force Electrosurgical Generators Instruction Manual," Valleylab Part No. 945 110 039 A, Feb. 1987, pp. 59–62.

Valleylab, Inc., "Advances in Bipolar Electrosurgery for Laparoscopic Surgery," Advances in Bipolar Electrosurgery, pp. 1–4.

Description of Codman and Johnson & Johnson Malis CMC–III Bipolar System.

Pfizer/Valleylab Press Release "Valleylab Inc. Introduces The Procision Bipolar Electrosurgery System," Sep. 15, 1994.

ArthroCare Corporation, "ArthroCare Arthroscopic Electrosurgery System, Model 970 Operator's Manual," Feb. 1996.

ArthroCare Corporation, "Arthroscopic Electrosurgery System, System 2000 Operator's Manual," Jan. 1998.

* cited by examiner

UNDER WATER TREATMENT

This application is a continuation of application Ser. No. 09/202,025, filed, Dec. 8, 1998, now U.S. Pat. No. 6,210,405 the entire content of which is hereby incorporated by reference in this application which is a 371 of PCT/GB97/01632 filed Jun. 17, 1997.

This invention relates to an electrosurgical instrument for the treatment of tissue in the presence of an electrically-conductive fluid medium, to electrosurgical apparatus including such an instrument, and to an electrode unit for use in such an instrument.

Endoscopic electrosurgery is useful for treating tissue in cavities of the body, and is normally performed in the presence of a distension medium. When the distension medium is a liquid, this is commonly referred to as underwater electrosurgery, this term denoting electrosurgery in which living tissue is treated using an electrosurgical instrument with a treatment electrode or electrodes immersed in liquid at the operation site. A gaseous medium is commonly employed when Endoscopic surgery is performed in a distensible body cavity of larger potential volume in which a liquid medium would be unsuitable, as is often the case in laparoscopic or gastroenterological surgery.

Underwater surgery is commonly performed using endoscopic techniques, in which the endoscope itself may provide a conduit (commonly referred to as a working channel) for the passage of an electrode. Alternatively, the endoscope may be specifically adapted (as in a resectoscope) to include means for mounting an electrode. or the electrode may be introduced into a body cavity via a separate access means at an angle with respect to the endoscope—a technique commonly referred to as triangulation. These variations in technique can be subdivided by surgical speciality, where one or other of the techniques has particular advantages given the access route to the specific body cavity. Endoscopes with integral working channels, or those characterised as resectoscopes are generally employed when the body cavity may be accessed through a natural body opening—such as the cervical canal to access the endometrial cavity of the uterus, or the urethra to access the prostate gland and the bladder. Endoscopes specifically designed for use in the endometrial cavity are referred to as hysteroscopes, and those designed for use in the urinary tract include cystoscopes, urethroscopes and resectoscopes. The procedures of transurethal resection or vaporisation of the prostate gland are known as TURP and EVAP respectively. When there is no natural body opening through which an endoscope may be passed, the technique of triangulation is commonly employed. Triangulation is commonly used during underwater endoscopic surgery on joint cavities such as the knee and the shoulder. The endoscope used in these procedures is commonly referred to as an arthroscope.

Electrosurgery is usually carried out using either a monopolar instrument or a bipolar instrument. With monopolar electrosurgery, an active electrode is used in the operating region, and a conductive return plate is secured to the patient's skin. With this arrangement, current passes from the active electrode through the patient's tissues to the external return plate. Since the patient represents a significant portion of the circuit, input power levels have to be high (typically 150 to 250 watts). to compensate for the resistive current limiting of the patient's tissues and, in the case of underwater electrosurgery, power losses due to the fluid medium which is rendered partially conductive by the presence of blood or other body fluids. Using high power with a monopolar arrangement is also hazardous, due to the tissue heating that occurs at the return plate. which can cause severe skin burns. There is also the risk of capacitive coupling between the instrument and patient tissues at the entry point into the body cavity.

With bipolar electrosurgery, a pair of electrodes (an active electrode and a return electrode) are used together at the tissue application site. Thus arrangement has advantages from the safety standpoint, due to the relative proximity of the two electrodes so that radio frequency currents are limited to the region between the electrodes. However, the depth of effect is directly related to the distance between the two electrodes; and, in applications requiring very small electrodes, the inter-electrode spacing becomes very small, thereby limiting tissue effect and the output power spacing the electrodes further apart would often obscure vision of the application site, and would require a modification in surgical technique to ensure direct contact of both electrodes with the tissue.

There are a number of variations to the basic design of the bipolar probe. For example, U.S. Pat. No. 4,706,667 describes one of the fundamentals of the design, namely that the ratio of the contact areas of the return electrode and of the active electrode is greater than 7:1 and smaller than 20:1 for cutting purposes. This range relates only to cutting electrode configurations. When a bipolar instrument is used for desiccation or coagulation, the ratio of the contact areas of the two electrodes may be reduced to approximately 1.1 to avoid differential electrical stresses occurring at the contact between the tissue and the electrode.

The electrical junction between the return electrode and tissue can be supported by wetting of the tissue by a conductive solution such as normal saline. This ensures that the surgical effect is limited to the needle or active electrode, with the electric circuit between the two electrodes beings completed by the tissue. One of the obvious limitations with the design is that the needle must be completively buried in the tissue to enable the return electrode to complete the circuit. Another problem is one of the orientation, even a relatively small change in application angle from the ideal perpendicular contact with respect to the tissue surface, will change the contact area ratio, so that a surgical effect can occur in the tissue in contact with the return electrode.

Cavity distension provides space for gaining access to the operation site, to improve visualisation and to allow for manipulation of instruments. In low volume body cavities, particularly where it is desirable to distend the cavity under higher pressure liquid rather than gas is more commonly used due to better optical characteristics, and because it washes blood away from the operative site.

Conventional underwater electrosurgery has been performed using a non-conductive liquid (such as 1.5% glycine) as an irrigant, or as a distension medium to eliminate electrical conduction losses. Glycine is used in isotonic concentrations to prevent osmotic changes in the blood when intra-vascular absorption occurs. In the course of an operation, veins may be severed, with resultant infusion of the liquid into the circulation, which could cause, among other things, a dilution of serum sodium which can lead to a condition known as water intoxication.

The applicants have found that it is possible to use a conductive liquid medium, such as normal saline, in underwater endoscopic electrosurgery in place of non-conductive, electrolyte-free solutions. Normal saline is the preferred distension medium in underwater endoscopic surgery when electrosurgery is not contemplated. or a non-electrical tissue effect such as laser treatment is being used. Although normal saline (0.9% w/v: 150 mmol/L) has an electrical conductivity somewhat greater than that of most body tissue, it has the advantage that displacement by absorption or extravasation from the operative site produces little physiological effect, and the so-called water intoxication effects of non-conductive, electrolyte-free solutions are avoided.

Carbon dioxide is the preferred gaseous distension medium, primarily because of its non-toxic nature and high water solubility.

In endoscopic procedures in which the distension medium is a gas, the applicants have found that it is possible to use an electrically-conductive gas (such as argon) in place of carbon dioxide. Argon is conductive when excited into a discharge state, and has been employed in both endoscopic and conventional monopolar electrosurgery as a method of increasing the distance between the tissue and the instrument, by providing a conductive path between the two when high voltage electrosurgical outputs such as spray or fulgurate are being used. The high voltages used in this application result in a very low penetration of the electrosurgical effect into the tissue, making the technique only suitable to control bleeding from multiple small blood vessels. This allows the surgeon to staunch bleeding from multiple sites in a surgical sites in a surgical wound using a rapid "painting" technique, rather than applying electrosurgery to each individual bleeding site. The argon gas is delivered through a hollow surgical instrument, and passes over the monopolar electrode exposed at the tip of the instrument as a stream. This produces a region at the operative site which is rich in argon, and which contributes to the distension of the body cavity. High voltage monopolar electrosurgical outputs are undesirable in endoscopic surgery, because of the risks of damaging structures outside the field of vision, by either capacitive or direct coupling to a portion of the instrument remote from the operative site often outside the field of vision of the operator.

The applicants have developed a bipolar instrument suitable for underwater electrosurgery using a conductive liquid or gaseous medium. This electrosurgical instrument for the treatment of tissue in the presence of a fluid medium comprises an instrument body having a handpiece and an instrument shaft and an electrode assembly, at one end of the shaft. The electrode assembly comprises a tissue treatment (active) electrode which is exposed at the extreme distal end of the instrument, and a return electrode which is electrically insulated from the tissue treatment electrode and has a fluid contact surface spaced proximally from the exposed part of the tissue treatment electrode. In use of the instrument, the tissue treatment electrode is applied to the tissue to be treated whilst the return electrode. being spaced proximally from the exposed part of the tissue treatment electrode, is normally spaced from the tissue and serves to complete an electrosurgical current loop from the tissue treatment electrode through the tissue and the fluid medium. This electrosurgical instrument is described in the specification of our European Patent Application 96918786.1

The electrode structure of this instrument, in combination with an electrically-conductive fluid medium, largely avoids the problems experienced with monopolar or bipolar electrosurgery. In particular, input power levels arc much lower than those generally necessary with a monopolar arrangement (typically 100 watts). Moreover, because of the relatively large spacing between its electrodes, an improved depth of effect is obtained compared with conventional bipolar arrangements.

The specification of our International Patent Application GB96/01472 describes an irritated bipolar electrosurgical instrument that can be used in open air or gas-filled environments This instrument includes an internal channel for feeding electrically-conductive fluid (typically saline) to the exposed end of a tissue treatment electrode so as to provide a conductive fluid path that completes an electrical circuit to a return electrode when the instrument is in use. This instrument also includes an internal channel for removing fluid from the region of the exposed end of the tissue treatment electrode. When the fluid is a liquid, such as saline, the presence of that liquid can cause collateral tissue damage, so its removal is desirable. This type of instrument is intended primarily for use in open air or Las-filled environments, and is not suitable for use with electrosurgical procedures which require distension of a body cavity.

However, where the volume of a body cavity is small— for example in arthroscope surgery where even the large joints, such as the knee, may only accommodate 50–60 ml of irrigation fluid—the following problems may occur, namely:

(i) Heated fluid in the immediate vicinity of the tissue contact electrode can cause collateral tissue damage;

(ii) The products of the tissue vaporized by the tissue contact electrode can cause visualisation problems; and (iii) Soft tissue present in anoint space tends to move about, making it difficult to apply the active electrode to vaporise such tissue.

An arthroscope electrode may be characterised as short (100 to 140 mm), and rigid with a working diameter up to 5 mm. It can be introduced through a stab incision into a joint cavity (with or without a cannula) using the triangulation technique. Such an electrode is operated with a motion which moves the electrode between the 9 O'Clock and 3 O'Clock positions on the arthroscopic image As a result, the tissue to be treated is usually approached at a shallow working angle with respect to the axis of the electrode. An arthroscopic electrode thus needs to have an effect consistent with this angled approach to the tissue The tissue to be treated, such as meniscal cartilage, is commonly dense and of a high electrical impedance. An arthroscope electrode requires output power and voltage settings that reflect the type of tissue being treated, the size of electrode, and the fact that arthroscopists are seeking a speed of effect comparable to that of the mechanical shaver devices they currently employ, albeit with an electrode of smaller dimensions than a shaver blade for improved access.

The aim of the invention is to provide an Improved electrosurgical instrument of this type.

The present invention provides a electrosurgical instrument for the treatment of tissue in the presence of an electrically-conductive fluid medium, the instrument comprising an instrument shaft. and an electrode assembly at one end of the shaft, the electrode assembly comprising a tissue treatment electrode and a return electrode which is electrically insulated from the tissue treatment electrode by means of an insulation member, the tissue treatment electrode having an exposed end for treating tissue, and the return electrode having a fluid contact surface which is spaced proximally from the tissue treatment electrode in such a manner as to define, in use, a conductive fluid path that completes an electrical circuit between the tissue treatment electrode and the return electrode, wherein the electrode assembly is provided with a plurality of apertures in the region of the tissue treatment electrode and distal to the return electrode, through which apertures vapour bubbles and/or particulate material can be aspirated from the region surrounding the tissue treatment electrode.

In a preferred embodiment, the instrument further comprises a pump for subjecting the distal end portion of the instrument shaft to a sub-atmospheric pressure thereby to aspirate, in use, vapour bubbles and/or particulate material through said apertures from the region surrounding the tissue treatment electrode.

Advantageously, the pump is activated cyclically whereby matter is aspirated in a pulsed fashion. The pump may additionally or alternatively be activated only when the tissue treatment electrode is powered for tissue vaporisation.

Preferably, the instrument further comprises an RF generator having a bipolar output connected to the tissue treatment electrode and the return electrode. In this case, the pump may be controlled in dependence upon the voltage output characteristics of the RF generator. In this way, the flow of vapour bubbles and/or aspirated particulate material is balanced to the voltage output characteristics of the RF generator to prevent excessive cooling of the tissue treatment electrode and a resultant increase in the vaporisation power threshold. The return electrode is spaced from the tissue treatment electrode so that, in use, it does not contact the tissue to be treated, and so that the electrical circuit is always completed by the conductive fluid, and not simply by arcing between the electrodes. Indeed, the arrangement is such that arcing between adjacent parts of the electrode assembly is avoided, thereby ensuring that the tissue treatment electrode can become enveloped in a vapour pocket so that tissue entering the vapour pocket becomes the preferred path for current to flow back to the return electrode via the conductive fluid.

The electrosurgical instrument of the invention is useful for dissection, resection, vaporisation, desiccation and coagulation of tissue, as well as for combinations of these functions. It has a particular application in arthroscopic surgery as it pertains to endoscopic and percutaneous procedures performed on joints of the body including, but not limited to, such techniques as they apply to the spine and other non-synovial joints. Arthroscopic operative procedures may include: partial or complete meniscectomy of the knee joint including meniscal cystectomy, lateral retinacular release of the knee joint, removal of anterior and posterior cruciate ligaments or remnants thereof, labral tear resection, acromioplasty, bursectomy and subacromial decompression of the shoulder joint; anterior release of the temperomandibular joint; synovectomy, cartilage debricement, chondroplasty, division of intra-articular adhesions, fracture and tendon debricement as applied to any of the synovial joints of the body, inducing thermal shrinkage of joint capsules as a treatment for recurrent dislocation, subluxation or repetitive stress injury to any articulated joint of the body; discectomy either in the treatment of a disc prolapse or as part of a spinal fusion via a posterior or anterior approach to the cervical, thoracic and lumbar spine or any other fibrous joint for similar purposes; excision of diseased tissue; and haemostasis.

The instrument of the invention is also useful for dissection, resection, vaporisation, desiccation and coagulation of tissue, as well as combinations of these functions, with particular application in urological endoscopic (urethroscopy, cystoscopy, ureteroscopy and nephroscopy) and percutaneous surgery. Urological procedures may include: electro-vaporisation of the prostate gland (EVAP) and other variants of the procedure commonly referred to as transurethal resection of the prostate (TURP) including but not limited to, interstitial ablation of the prostate gland by a percutaneous or perurethral route whether performed for benign or malignant disease; transurethal or percutaneous resection of urinary tract tumours as they may arise as primary or secondary neoplasms, and further as they may arise anywhere in the urological tract from the calyces of the kidney to the external urethral meatus; division of strictures as they may arise at the pelviureteric junction (PUJ), ureter, ureteral orifice, bladder neck or urethra; correction of ureterocoele, shrinkage of bladder diverticular, cystoplasty procedures as they pertain to corrections of voiding dysfunction; thermally induced shrinkage of the pelvic floor as a corrective treatment for bladder neck descent, excision of diseased tissue, and haemostasis.

Surgical procedures using the electrosurgical instrument of the invention may also include introducing the electrode assembly to the surgical site, whether through an artificial conduit (a cannula) or a natural conduit, which may be in an anatomical body cavity or space, or one created surgically. The cavity or space may be distended during the procedure using a fluid, or may be naturally held open by anatomical structures. The surgical site may be bathed in a continuous flow of conductive fluid such as saline solution either to fill and distend the cavity, or to create a locally-irrigated environment around the tip of the electrode assembly in a gas filled cavity. The irrigating fluid may be aspirated from the surgical site to remove products created by application of the RF energy, tissue debris or blood. The procedures may include simultaneous viewing of the site via an endoscope, or using an indirect visualisation means. An irrigated bipolar electrosurgical instrument is described in the specification of our International Patent Application GB96/01471

Advantageously, the exposed end of the tissue treatment electrode extends laterally through a cut-out provided in the insulation member at the distal end portion of the instrument, the fluid contact surface of the return electrode overlying the insulation member in the region of the cut-out.

In a preferred embodiment, a single coiled filament constitutes the tissue treatment electrode, and said apertures are formed in the insulation member, the apertures being positioned around, and adjacent to, the tissue treatment electrode. Preferably, the filament has a diameter lying within the range of from 0.05 mm to 1.0 mm.

Alternatively, an apertured plate constitutes the tissue treatment electrode, the apertures of the plate constituting the apertures through which vapour bubbles and/or particulate material can be aspirated. The outer surface of said plate may be formed with recesses adjacent to the apertures. The recesses trap vapour pockets and so reduce the vaporisation power threshold of the instrument.

The tissue treatment electrode may be made of tungsten or of an alloy of tungsten or platinum.

Preferably, the instrument further comprises a tube positioned within the instrument shaft for connecting said apertures to the pump. The tube may be a multi-lumen tube, in which case it defines a plurality of channels, the diameter of each of said channels being at least equal to the diameter of the apertures in the region of the tissue treatment electrode. Alternatively, the instrument further comprises a filter at the distal end of the tube.

The invention also provides an electrode unit for an electrosurgical instrument for the treatment of tissue in the presence of an electrical-conductive fluid medium, the electrode unit comprising a shaft having at one end means for connection to an instrument handpiece. and, mounted on the other end of the shaft. an electrode assembly comprising a tissue treatment electrode and a return electrode which is electrically insulated from the tissue treatment electrode by means of an insulation member, the tissue treatment electrode having an exposed end for treating tissue, and the return electrode having a fluid contact surface which is spaced from the tissue treatment electrode in such a manner as to define, in use, a conductive fluid path that completes an electrical circuit between the tissue treatment electrode and the return electrode, wherein the electrode assembly is provided with a plurality of apertures in the region of the tissue treatment electrode, through which apertures vapour bubbles and/or particulate material can be aspirated from the region surrounding the tissue treatment electrode.

The invention further provides electrosurgical apparatus comprising a radio frequency generator and an electrosurgical instrument for the treatment of tissue in the presence of an electrically-conductive fluid medium, the instrument comprising an instrument shaft, and an electrode assembly at one end of the shaft, the electrode assembly comprising a tissue treatment electrode and a return electrode which is electrically insulated from the tissue treatment electrode by means of an insulation member, the tissue treatment electrode having an exposed end for treating tissue, and the return electrode having a fluid contact surface which is spaced from the tissue treatment electrode in such a manner as to define, in use, a conductive fluid path that completes an electrical circuit between the tissue treatment electrode and the return electrode, and the radio frequency generator having a bipolar output connected to the electrodes, wherein the electrode assembly is provided with a plurality of apertures in the region of the tissue treatment electrode, through which apertures vapour bubbles and/or particulate material can be aspirated from the region surrounding the tissue treatment electrode.

The invention will now be described in greater detail, by way of example, with reference to the drawings, in which.

Figure 1:
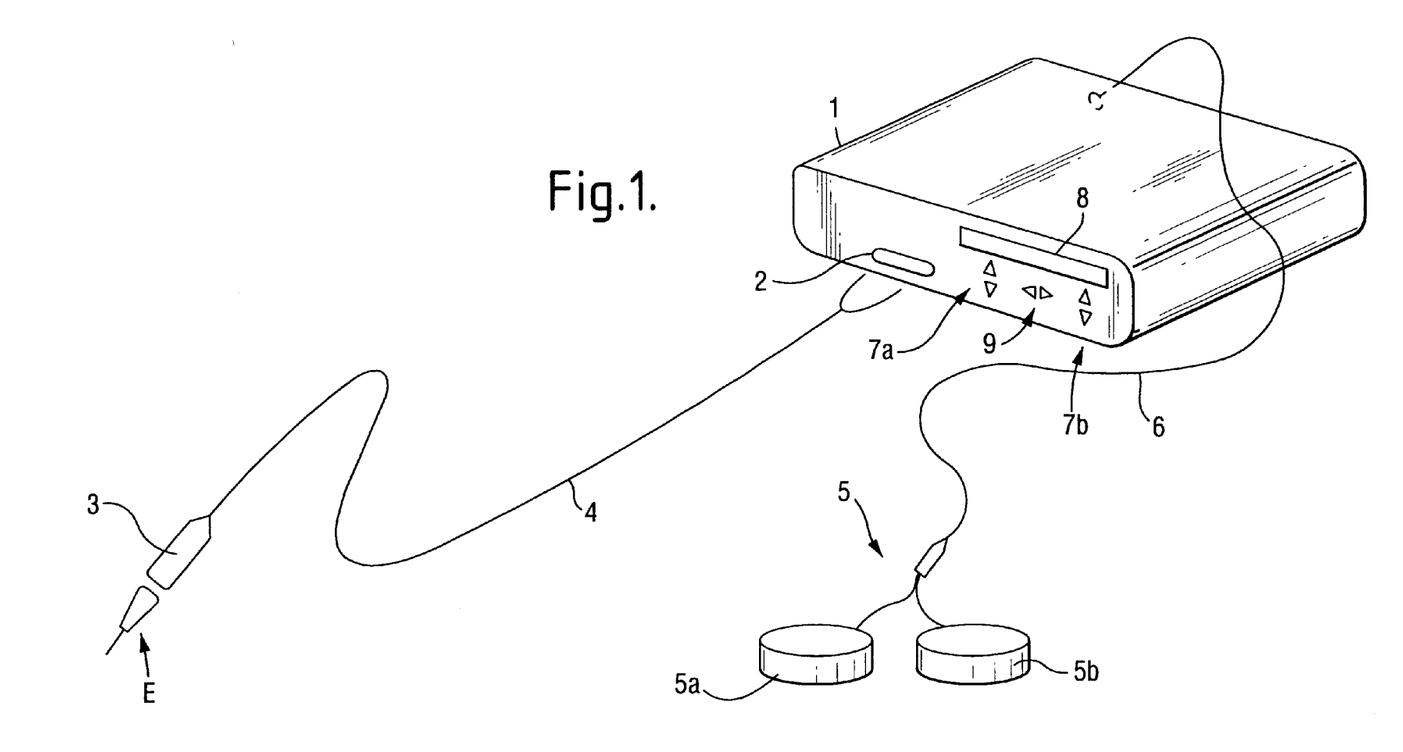
FIG. 1 is a diagram showing an electrosurgical apparatus constructed in accordance with the invention.

Referring to the drawings, FIG. 1 shows electrosurgical apparatus including a generator 1 having an output socket 2 providing a radio frequency (RF) output, via a connection cord 4, for an instrument in the form of a handpiece 3. Activation of the generator 1 may be performed from the handpiece 3 via a control connection (not shown) in the cord 4, or by means of a footswitch unit 5 connected separately to the rear of the generator 1 by a footswitch connection cord 6. In the illustrated embodiment, the footswitch unit 5 has two footswitches 5a and 5b for selecting a desiccation mode and a vaporisation mode of the generator 1 respectively. The generator front panel has push buttons 7a and 7b for respectively setting desiccation and vaporisation power levels, which are indicated in a display 8. Push buttons 9 are provided as an alternative means for selection between the desiccation and vaporisation modes.

The handpiece 3 mounts a detachable electrode unit E, such as the electrode units E1 to E4 to be described below.

Figure 2:
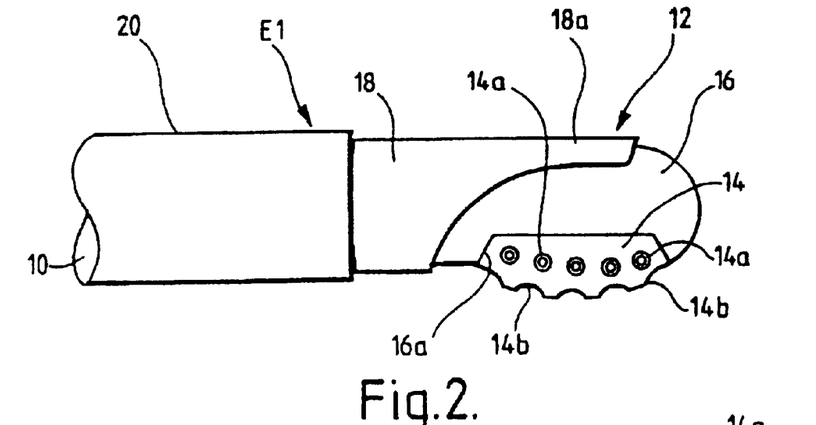
FIG. 2 is a diagrammatic side elevation of a first form of electrode unit constructed in accordance with the invention.

FIG. 2 shows the first form of electrode unit E1 for detachable fastening to the electrosurgical instrument handpiece 3, the electrode unit comprising a shaft 10, which is constituted by a semi-flexible tube made of stainless steel or phynox electroplated in copper or gold. with an electrode assembly 12 at a distal end thereof At the other end (not shown) of the shaft 10, means are provided for connecting the electrode unit E1 to the handpiece 3 both mechanically and electrically The RF generator 1 (not shown in FIG. 2) delivers an electrosurgical current to the electrode assembly 12. The generator 1 includes means for varying the delivered output power to suit different electrosurgical requirements. The generator may be as described in the specification of our European Patent Application 96304558.8.

The electrode unit E1 includes an active (tissue treatment) electrode 14 which is constituted by a curved fenestrated plate made of tungsten or an alloy of tungsten or platinum. The active electrode 14 is formed with a plurality of fenestrations 14a, and the regions 14b of the active electrode adjacent to the fenestrations define cup-shaped recesses (see FIG. 3). The active electrode 14 is connected to the RF generator 1 via an insulated central copper conductor (not shown). A ceramic insulation sleeve 16 surrounds the central conductor, the active electrode 14 extending laterally therefrom through a cut-out 16a. A polytetrafluoroethylene, a polyolelin, a polyester or ethylene tetrafluoroethvlene) surrounds the proximal portion of the shaft adjacent to the return electrode 18. The return electrode 18 is formed with a hood-like extension 18a which extends over the surface or the sleeve 16 which is opposite to the cut-out 16a. The electrode unit E1 can, thus, provide maximum tissue engagement for shallow working angle applications, and is known as a side-effect electrode.

This electrosurgical instrument is particularly useful for rapid tissue debunking. One of the problems which could be encountered when tissue is rapidity debunked using an arthroscopic electrode configuration, particularly when working in small joint spaces, is the production of vapour bubbles generated as an end product of tissue vaporisation Such bubbles obscure vision, and can coaiesce at the site of tissue application, so that the electrical circuit between the active and return electrodes becomes compromised by the absence of conductive fluid. Irregular active electrodes having filamentary, mesh or coiled spring forms go some way to solving this problem, as they reduce the vaporisation threshold as disclosed in the specification of our International Patent Application GB97/00065. Another advantage of these electrode forms is that the bubbles generated by vaporisation are smaller than those formed by solid electrodes. As the brush electrode 14 of this electrosurgical instrument s of irregular shape, it also has the advantage of producing relatively small vapour bubbles as the product of tissue vaporisation. The production of vapour bubbles is, however, further reduced as a result of the lower threshold power of vaporisation which results from use of the electrode unit E1. This improvement results from the hood-like extension 18a of the return electrode 18 which extends over the back of the active electrode 14. This reduces the separation between the active electrode 14 and the return electrode 18, thereby reducing the electrical field and the vaporisation threshold power of the active electrode. This enhances the speed of vaporisation of the tissue at a lower power than would otherwise be required for the given active electrode area, and hence reduces the formation of vapour bubbles. As the hood-like extension 18a extends along the entire length of the active electrode 14, a large active electrode size can be supported, despite the reduction in electrode separation. 18a extends along the entire length of the active electrode 14, a large active electrode size can be supported, despite the reduction in electrode separation.

In order to reduce further the problems of vapour bubble production, the electrode unit E1 is provided with a suction pump (not shown) which can remove vapour bubbles via the shaft of the instrument through the fenestrations 14a in the active electrode 14. This enhances the elimination of vapour bubbles from an operation site, which is particularly advantageous during aggressive tissue debulking. The suction pump must be controlled so that the flow of bubbles through the electrode 14 is balanced to the voltage output characteristics of the RF generator 1 to prevent excessive cooling of the active electrode and a resultant increase in its vaporisation power threshold. The thermal mass of the fenestrated active electrode 14 is lower than that of a solid form active electrode, and this assists in rapidly reestablishing the vapour pocket around the active electrode should this collapse following excessive cooling. The cup-shaped recesses 14b in the active electrode 14 help to maintain the vapour pocket by retaining saline despite the fluid flow caused by the aspiration of the suction pump. The trapped saline absorbs energy, and so is vaporized in preference to the saline in the fluid flow caused by the aspiration.

The robustness of the electrode assembly 12 is also important In arthroscopic surgery, both because of the tendency of surgeons to use an electrode assembly as a cold manipulator, and because of the rigid nature of the tissue to be treated—particularly bone and cartilage The hood-like extension 18a adds mechanical strength to the electrode assembly 12, as it extends over the ceramic insulation sleeve 16, thereby reducing the risk of ceramic fracture and potential breakdown of insulation.

The electrode unit E1 is intended primarily for use in arthroscopic surgery which requires rapid tissue debulking by vaporisation. In use, the electrosurgical instrument is manipulated to introduce the electrode assembly 12 into a selected operation site (for example, within the joint space of a knee), so that the electrode 14 contacts the tissue to be treated, and with the tissue and the electrode assembly immersed in saline.

The footswitch 5b (or the push button 7b) is then operated to set the required power level for vaporisation. The generator 1 then provides sufficient RF power to the electrode assembly 12 to vaporise the saline surrounding the electrode 14, and to maintain a vapour pocket surrounding this electrode. Using a brushing technique, with firm pressure against the tissue surface, rapid debulking of the tissue is achieved. Gently touching the tissue will reduce the effect, and can be used to sculpture and smooth the residual tissue surface. With tissue engagement, provided the geometry of the active electrode 14 is appropriate for the application, the flow of irrigant through the active electrode will be reduced, the amount of reduction depending on the nature of the tissue surface, the application pressure and the suction pressure. Speed of debulking will, therefore, depend on these variables. Once the vaporisation occurs, the products will include vapour bubbles, carbon particles and tissue debris. All of these products are removed from the region of the action electrode 14 by aspiration caused by the suction pump. The fenestrations 14a are positioned so that vaporized tissue is drawn into the instrument, and then evacuated through the instrument shaft 10, by the aspiration of the suction pump.

The electrode unit E1 is also very, effective in removing heated saline (distension fluid) from within a joint cavity. The risk of hot distension fluid occurs primarily during power application to reach the vaporisation threshold. Once the threshold has been reached, the power requirement falls by 30–50%.

Whilst aspiration through the active electrode 14 will remove heated saline from the body cavity, and remove any risk of overheating through prolonged activation under conditions where the vaporisation threshold is not reached, the cooling effect and disruption of vapour pockets created around the active electrode will increase the vaporisation threshold. A vicious cycle can, therefore, be created, wherein the more suction applied through the electrode 14, the more power required to reach the vaporisation threshold, and the greater the risk of heating. The other factor influencing the vaporisation threshold is the ratio of return active contact area, and the insulation separation between the two electrodes 14 and 18. The size of the active electrode 14 and the insulation separation must, therefore, be reduced to the minimum necessary to achieve the function in order to offset the effects of aspiration in elevating the power threshold of vaporisation.

The specification of our International Patent Application GB97/00065 discloses techniques for controlling the vaporisation threshold by employing active electrode designs which assist in capturing vapour pockets and preventing cooling of the active electrode application site by screening from the flow of irrigant provided by channels in an endoscope. The fenestrated electrode 14 of FIG. 2, which is reminiscent of a grater in which the holes are punched outwards from the inside, provides both the aspiration holes 14a and the areas 14b where the vapour pockets may be trapped, to reduce the vaporisation power threshold.

An alternative or supplementary method of reducing the vaporisation power threshold is to pulse the suction pressure, thereby allowing the threshold to be attained between pulses. Such pulses may be synchronised with the output features of the RF generator 1, both for safety reasons (if there is an occlusion of the suction channel), and to provide power bursts during active suction to sustain the vapour pocket, and clear any tissue occluding the fenestrations 14a in the active electrode 14.

A known technique in arthroscopic surgery is to apply suction through a mechanical tissue-ribbling device, so that soft tissue present in the joint space, such as the infrapatellar fat pad, can be held in position within the nibbler jaws by suction whilst it is progressively "nibbled" away.

Attracting tissue to the active electrode 14 of the electrode unit E1 has a similar effect as, for the reasons already given above, compliant tissue adhering to the active electrode will result in a reduction of the vaporisation power threshold. Adherent tissue will be rapidly vaporised, and small issue particles produced during vaporisation will be aspirated from the application site.

Because of its speed of debulking and side-effect configuration, the electrode unit E1 also has advantages in urological surgery as an EVAP technique for use in conjunction with a resectoscope. A resectoscope electrode unit is introduced very differently, in that it is mounted on an endoscope prior to passage of the assembled instrument through a working sheath introduced via the urethra. The proximal end of the electrode unit is connected to a trigger assembly and an electrical contact which is integral with the resectoscope. By this means, the electrode unit E1 can be moved back and forth through a defined range of motion by operating the trigger mechanism. As the electrode unit E1 is assembled prior to introduction, the size of the tip is not constrained by working channel dimensions, but rather by the diameter of the working sheath which can be up to 10 mm. Part of this diameter is occupied by the support wires to the electrode unit E1, which wires are commonly bent in a downward angle, with respect to the endoscopic image, to the working rip, so that they do not interfere with either visualisation or its operation. The electrode 14 can have a length lying, within the range of from 3 mm to 4 mm and a width lying in the range of from 2 mm to 3 mm, and this size is necessary to urological surgery given that, on average, 20–30 grams of prostate tissue must be removed.

Because of the reservoir effect of the urinary bladder, and the mounting of the endoscope to view the rip of the active electrode 14 from below, bubble generation during vaporisation is less to a problem during endoscopic urology, as the bubbles flow away from the endoscope to accumulate in the bladder Nevertheless, the use of the electrode unit E1 substantially reduces the possibility of bubble generation causing problems.

Although the electrode unit E1 is intended primarily for use in the vaporisation of tissue, it can also be used for desiccation, particularly of synovial membranes or to separate muscle attachments. In this case, once the electrode assembly 12 has been introduced into a selected operation site, the RF generator 1 is actuated using the footswitch 5a or the push button 7a to set the required power level for desiccation. The generator 1 will then provide sufficient RF power to the electrode assembly 12 to maintain the saline adjacent to the fenestrated electrode 14 substantially at its boiling point without creating a vapour pocket surrounding that electrode. The instrument can then be manipulated by moving the electrode 14 across the surface of the tissue to be treated in a side-to-side "painting" technique.

The electrode unit E1 can also be used for delivering a blended power output. This is achieved by automatically alternating the output of the RF generator 1 between the desiccation and vaporisation power levels, so that more haemostasis is produced then is possible in the vaporisation mode. As a consequence, the speed of tissue debulking is reduced, but the increased haemostasis is useful when cutting or debulking vascular tissue structures. Alternatively, the output of the RF generator 1 can be pulsed at the vaporisation power level, without cycled activation of the desiccation mode. This produces a less aggressive tissue vaporisation than occurs in the vaporisation mode, with a consequent reduction in both bubble formation and the risk of tissue charring.

Figure 4:
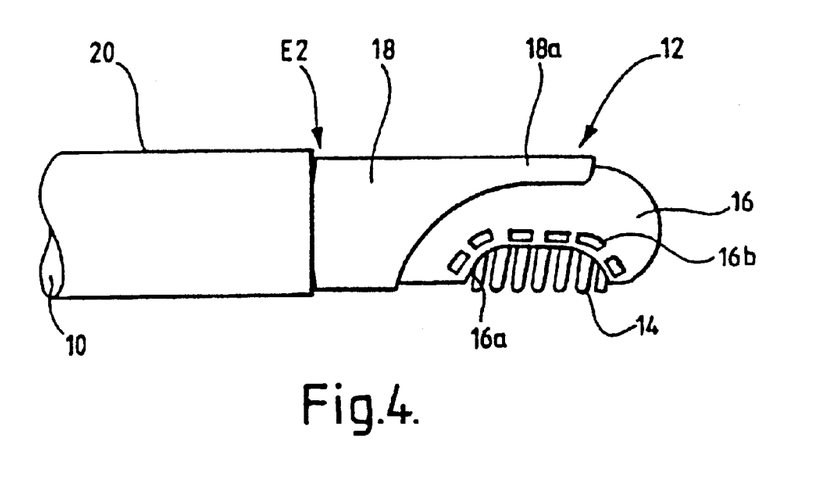
FIGS. 4 to 6 are diagrammatic side elevations of second, third and fourth forms of electrode unit constructed in accordance with the invention.
Figure 5:
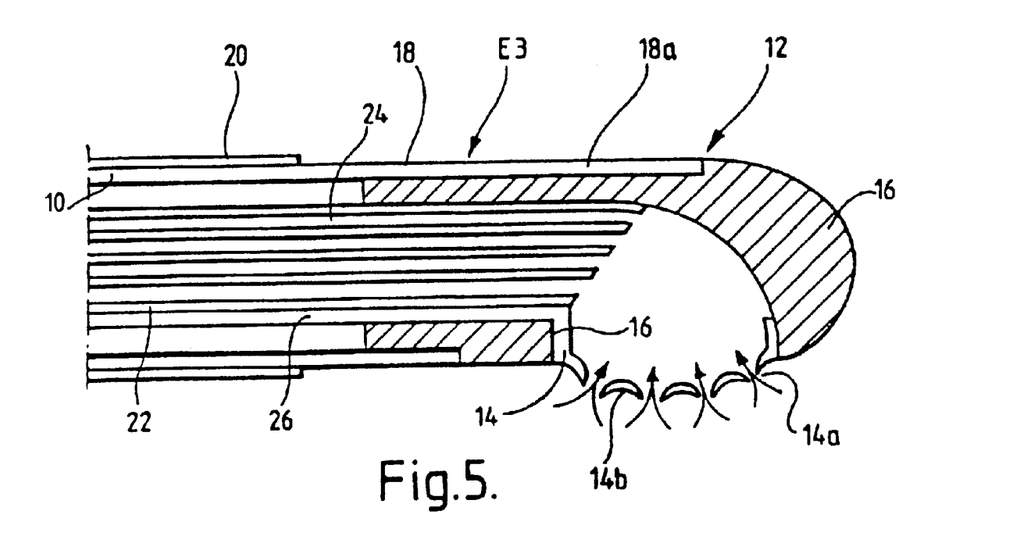
Figure 6:
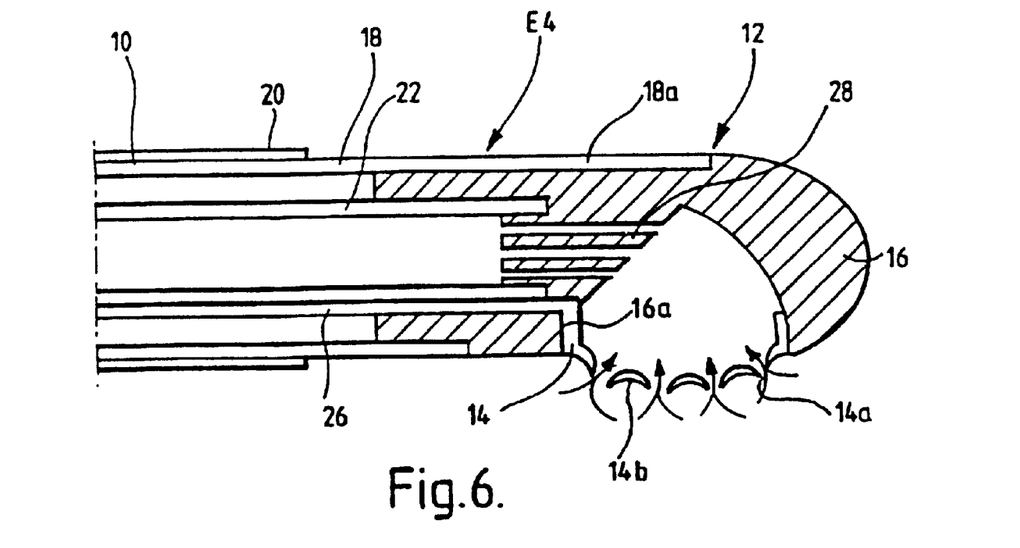

FIGS. 4 to 6 show electrode units E2 to E4 which are modified versions of the electrode unit E1. Accordingly, like reference numerals will be used for like parts, and only the modifications will be described in detail. Thus, the active electrode 14 of the electrode unit E2 is a coiled spring electrode mounted within the cut-out 16a. The coiled spring electrode 14 is made of tungsten or an alloy of tungsten or platinum, and its proximal end is connected to the RF generator 1 via an insulated central copper conductor (not shown). The electrode unit E2 is, however, provided with fenestrations 16b formed in the insulation sleeve 16, the fenestrations 16b being positioned all around, and adjacent to, the active electrode 14. These fenestrations 16b constitute the aspiration pathway for vapour bubbles, tissue and debris to be extracted, thereby enhancing the establishment of vapour pockets on the active electrode surface, and the inclusion of good vaporisation threshold properties, whilst ensuring good extraction of heated saline. The fenestrations 16b are positioned sufficiently close to the active electrode 14 to ensure that substantially all vaporised tissue is drawn into the instrument, and then evacuated through the instrument shaft 10, by the aspiration of the suction pump. In a modified version of this embodiment, the adjacent turns of the coiled spring electrode could define additional fenestrations for assisting with the aspiration of vapour bubbles, carbon particles and tissue debris.

Figure 3:
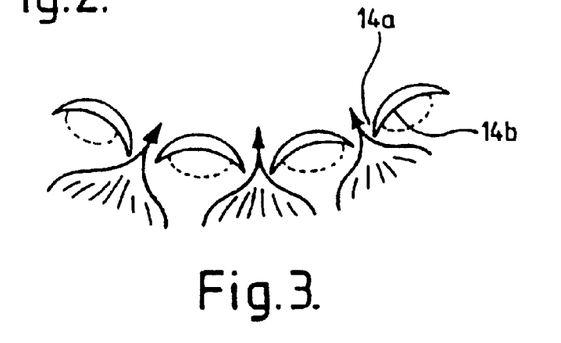
FIG. 3 is an enlarged view, looking in the direction of the arrow A of FIG. 2 of part of the first form of electrode unit.

The electrode unit E3 of FIG. 5 has a "grater" active electrode 14 similar to that of FIGS. 2 and 3 The instrument shaft 10 contains a multi-lumen tube 22 which defines a plurality of aspiration channels 24. The active electrode 14 is connected to the RF generator 1 by means of an insulated copper conductor 26. This embodiment has the advantage that, if a bolus of saline obstructs one or more of the channels 24, vapour can still be aspirated through the residual "open" channels 24. In this case, the bore of each channel 24 must not be narrower than the fenestrations 14a in the active electrode 14, thereby preventing obstruction of the channels by particulate debris generated at the tissue application site.

The electrode unit E4 of FIG. 6 includes a single-lumen tube 22 provided with an integral filter 28 at the distal end thereof. The filter 28 prevents obstruction of the lumen tube A2 by particulate debris generated at the tissue application site. Alternatively, the filter 28 could be formed integrally within the insulation sleeve 16 at the distal end of the tube 22. Again, the filter 28 could comprise a mesh having a small pore size for preferentially allowing de-gassing of the vaporisation products whilst accumulating solid material on the filter. In this case, gaseous extraction will be facilitated by the fact that the proximal single-lumen aspiration tube 22 can be constructed to withstand large vacuum pressures without collapsing. Here again, the active electrode 14 is connected to the RF generator 1 by means of an insulated copper conductor 26.

Each of the electrode units E1 to E4 has the additional advantage that the aspiration in the region of the active electrode 14 restricts the flow of convection currents in the saline surrounding the electrode assembly 12. As the power threshold required to reach vaporisation is dependent on the power dissipation of the active electrode 14 and the flow characteristics around it, the power threshold is dependent upon the maximum rate of convection. Consequently, the restriction of the convection currents reduces the power threshold, and this is advantageous as it enables the use of a cheaper RF generator, as well as avoiding problems such as dissipation within the instrument, and catastrophic overheating of the active electrode. It also facilitates control of the generator once vaporisation commences. The importance of power threshold of vaporisation is discussed in greater detail in the specification of our International Patent Application GB97/00065.

Another advantage of these electrode units is that, in use, the active electrode 14 faces down, so that saline heated thereby rises to the return electrode 18. This leads to a reduction of impedance throughout the circuit, and hence to a reduction of the heat dissipation in the saline path.

It will be apparent that modifications could be made to the embodiments described above For example, the lumen tubes 22 of the embodiments of FIGS. 5 and 6 could be used with the electrode assembly 12 of FIG. 4, that is to say with the fenestrated insulation sleeve embodiment. It would also be possible to make the insulation sleeve 16 of each of the embodiments of a silicone rubber (such as a silicone polyurethane), glass, a polyimide or a thermoplastics material.

Throughout this specification, the term "pump" should be construed to include any suitable controlled vacuum source.

What is claimed is:

1. An electrosurgical instrument for the treatment of tissue in the presence of an electrically-conductive fluid medium, the instrument comprising an instrument shaft, and an electrode assembly at one end of the shaft, the electrode assembly comprising a tissue treatment electrode and a return electrode which is electrically insulated from the tissue treatment electrode by means of an insulation member, the tissue treatment electrode having an exposed surface for treating tissue, and the return electrode having a fluid contact surface which is spaced proximally from the tissue treatment electrode in such a manner as to define, in use, a conductive fluid path that completes an electrical circuit between the tissue treatment electrode and the return electrode, wherein the electrode assembly is provided with at least one aperture in the region of the tissue treatment electrode through which vapour bubbles and/or particulate material can be aspirated from the region surrounding the tissue treatment electrode, and a plurality of fluid pathways leading to the aperture formed by the tissue treatment electrode.

2. An electrosurgical instrument as recited in claim 1, further comprising an RF generator having a bipolar output connected to the tissue treatment electrode and the return electrode.

3. An electrosurgical instrument as recited in claim 1, wherein the tissue treatment electrode is comprised of at least one filament.

4. An electrosurgical instrument as claimed in claim 1, wherein said aperture is formed in the insulation member, the aperture being adjacent to the tissue treatment electrode.

5. An electrosurgical instrument as recited in claim 1, wherein the tissue treatment electrode is comprised of a plurality of filaments connected to one another.

6. An electrode unit as recited in claim 1, wherein the plurality of fluid pathways leading to the aperture are formed by a plurality of fenestrations in the tissue treatment electrode.

7. An electrode unit for an electrosurgical instrument for the treatment of tissue in the presence of an electrically-conductive fluid medium, the electrode unit comprising a shaft having at one end means for connection to an instrument handpiece, and, mounted on the other end of the shaft, an electrode assembly comprising a tissue treatment electrode and a return electrode which is electrically insulated from the tissue treatment electrode by means of an insulation member, the tissue treatment electrode having an exposed end for treating tissue, and the return electrode having a fluid contact surface which is spaced proximally from the tissue treatment electrode in such a manner as to define, in use, a conductive fluid path that completes an electrical circuit between the tissue treatment electrode and the return electrode, wherein the electrode assembly is provided with a plurality of fluid pathways formed by the tissue treatment electrode leading to at least one aperture in the region of the tissue treatment electrode and distal to the return electrode, through which aperture vapour bubbles and/or particulate material can be aspirated from the region surrounding the tissue treatment electrode.

8. An electrode unit as recited in claim 7, further comprising an RF generator having a bipolar output connected to the tissue treatment electrode and the return electrode.

9. An electrode unit as recited in claim 7, wherein the tissue treatment electrode is comprised of at least one filament.

10. An electrode unit as recited in claim 7, wherein the tissue treatment electrode is comprised of a plurality of filaments connected to one another.

11. An electrode unit as recited in claim 7, wherein the plurality of fluid pathways leading to the aperture are formed by a plurality of fenestrations the tissue treatment electrode.

* * * * *